US005618386A

United States Patent [19]
Arbeloa et al.

[11] Patent Number: 5,618,386
[45] Date of Patent: Apr. 8, 1997

[54] ENZYMATIC BLEACHING OF CHEMICAL LIGNOCELLULOSE PULP

[75] Inventors: Marguerite Arbeloa, Villenave D'Ornon; Joël de Leseleuc, Merignac; Gérard Goma, Ramonville-St-Agne; Jean-Claude Pommier, Gradignan, all of France

[73] Assignee: La Cellulose Du Pin, Bordeaux, France

[21] Appl. No.: 457,793

[22] Filed: Jun. 1, 1995

Related U.S. Application Data

[63] Continuation of Ser. No. 64,801, May 21, 1993, abandoned, which is a continuation of Ser. No. 826,415, Jan. 27, 1992, abandoned.

[30] Foreign Application Priority Data

Jan. 25, 1991 [FR] France .................... 91 00870

[51] Int. Cl.$^6$ ................ D21C 3/20; D21C 9/10
[52] U.S. Cl. ............... 162/72; 435/277; 435/278
[58] Field of Search ............ 435/72, 277, 278; 162/72

[56] References Cited

U.S. PATENT DOCUMENTS 4,478,747  10/1984  Crawford et al. .............. 435/72

FOREIGN PATENT DOCUMENTS 0244262  11/1987  European Pat. Off. .
0371712  6/1990  European Pat. Off. .
0386888  9/1990  European Pat. Off. .............. 162/72

OTHER PUBLICATIONS

Abstract Bulletin of the Institute of Paper Chemistry vol. 5, No. 8. Fevrier 1988, Appleton US P. 1038; Ramachandra, M.: Crawford, D. L.; Pometto, A.L.; "Extracellular enzyme activities during lignocellulose degradation by Streptomyces spp: comparative study of wild–type and genetically ...".

Primary Examiner—Steven Alvo
Attorney, Agent, or Firm—Oblon, Spivak, McClelland, Maier & Neustadt, P.C.

[57] ABSTRACT

A process for treating lignocellulose pulp using a preparation containing at least one enzyme that produces a solubilizing action and, potentially, a hemicellulolytic action on lignin. The enzymes are derived from the bacterium *Streptomyces viridosporus*. This enzymatic treatment may be used for the separation of lignin from lignocellulose pulp in a procedure, for example, that complements a bleaching treatment.

9 Claims, 1 Drawing Sheet

ENZYMATIC BLEACHING OF CHEMICAL LIGNOCELLULOSE PULP

This application is a continuation of application Ser. No. 08/064,801, filed on May 21, 1993, which is a continuation of application Ser. No. 07/826,415, filed on Jan. 27, 1992, now both abandoned.

BACKGROUND OF THE INVENTION

1. Field of the Invention

The present invention relates to a process for treating lignocellulose pulp using a preparation containing at least one enzyme that produces a solubilizing action and, potentially, a hemicellulolytic action on lignin. The enzymes are derived from the bacterium *Streptomyces viridosporus*.

This enzymatic treatment may be used for the separation of lignin from lignocellulose pulp in a procedure, for example, that complements a bleaching treatment.

2. Background Information

The present invention relates to the enzymatic treatment of chemical lignocellulose pulps used in the paper industry.

These pulps are obtained from wood, which is composed essentially of a fibrous matrix of cellulose and hemicellulose, as well as lignin, whose complex macromolecular structure is similar to the fibrous matrix.

The presence of lignin causes certain difficulties. In particular, lignin is sensitive to ultraviolet light, causing formation of brownish products which are not highly valued and which impair the whiteness normally sought in white paper products.

For this reason, the paper industry attempts to eliminate all or a portion of the lignin. This elimination process utilizes chemical treatments; thus, the pulp obtained is a chemical pulp.

When white paper is produced, supplementary treatments, called bleaching treatments, prove necessary. These processes generally encompass several steps, including, in particular, delignification under oxygen (step O); chlorination procedures using chlorine $Cl_2$ (step C), chlorine dioxide (step D), or a mixture of the two (steps C/D), where the percentage of substitution of $ClO_2$ for $Cl_2$ may reach 50 to 100%; and hypochlorite-reaction steps (steps H).

In addition, alkaline-extraction procedures (steps E), potentially enhanced under oxygen (steps (E/O), may also be implemented.

Thus, currently-used bleaching procedures involve the following steps in succession using the abbreviations designated above as:

C-E-H-D or C/D-E-D-E-D or O-C/D-E/O-D-E-D.

However, this chlorine reaction procedure produces by-products such as chlorolignins which biodegrade only slightly and may be toxic, and which at certain concentrations may pollute the environment when drained away as effluents.

Alternative procedures are now available which use, for example, ozone and/or hydrogen peroxide; however, the whiteness of the resulting paper needs further improvement.

The problems addressed by Applicants and others in the field were to obtain a pulp having at least the equivalent degree of whiteness using fewer chlorinating agents when bleaching procedures containing chlorinating agents were used, and in cases of bleaching procedures where chlorinating agents were not utilized, to improve the final whiteness in the product.

Others in the field have examined the use of enzymatic preparations derived from microorganisms in treatments that separate lignin from the lignocellulose pulp. The principal part of these protocols focusing on the fungal enzymes are described below.

Patents U.S. Pat. No. 4,690,895 and EP-A-345 715 both describe delignification of kraft pulps using an enzymatic preparation derived from the fungus *Phanerochaete chrysosporium*.

U.S. Pat. No. 4,690,895 describes a mutant of this fungus which produces lignases, specifically, peroxidases which makes it possible to decompose the aromatic compounds in the lignin.

The treatment requires pulp to be in a solution having an acidic pH of between 2 and 7, and preferably 4.5, enriched with oxygen and fed with hydrogen peroxide in the presence of manganese sulfate. Incubation lasts for 12 h at 39° C.

A second incubation using sodium carbonate must then be carried out before decanting the pulp and washing it in water.

In Patent Application EP-A-345 715, the enzymes described are also lignins-peroxidases and/or lignins-peroxidases combined with manganese which has a degree of oxidation of 2 (Mn II). The enzymatic conditions in this treatment are similar to U.S. Pat. No. 4,690,895, the difference being the additional presence of a detergent and another compound such as an α-hydroxylated acid. The preferred manner of implementing the procedure consists in an alkaline extraction, washing in water, followed by an acid extraction.

Patent Application EP-A-371 712 studies the gene responsible for the formation of the lignin-peroxidase enzyme in the DNA structure of the bacterium *Streptomyces viridosporus*. According to this application, the enzyme makes it possible to oxidize the lignin in the presence of hydrogen peroxide having an acidic pH.

In accordance with a slightly different procedure, Patent Application EP-A-373 107 proposes a treatment using hemicellulases which are enzymes derived form the fungus *Aureobasidium pullulans*. Hemicellulase displaces the lignin which is covalently bonded by decomposing the hemicellulase and the lignin is separated by alkaline extraction. The treatment may also be carried out at an acidic pH, i.e., of approximately 5.

In a similar manner, Patent Applications EP-A-383 999 and EP-A-395 792 propose the use of enzymes in general to treat the pulps, and in particular, hemicellulases derived from bacteria belonging to the Streptomyces family are disclosed.

However, these methods proposing treatment with hemicellulase may cause problems. Hemicellulase has no specific action on lignin and tends to decompose not only the hemicellulose bonded covalently to the lignin, but also acts on hemicelluloses not bonded to the lignin, which is not the objective sought. The portion of the hemicellulose not bonded to the lignin but yet solubilized by these enzymes may cause a certain reduction in yield. Furthermore, it may increase the biochemical oxygen demand (BOD) of the reactive medium, a portion of which becomes effluents in the environment.

Thus, it appears that the only fungal or bacterial enzymes known for their specific action on lignin are peroxidases. The treatment of a lignocellulose pulp using preparations based on such enzymes implies the obligatory presence of a co-substrate such as hydrogen peroxide, and even the presence of additional agents.

The only alternative is to use hemicellulases, whose disadvantages have already been mentioned.

Furthermore, it has been found that in most of the types of enzymatic preparations mentioned above, a substantial acidic pH is recommended. But, after undergoing alkaline chemical treatment during baking and/or bleaching, the pulps have a basic pH greater than 8 in aqueous suspension. This implies that if one desires to treat the pulp after an alkaline treatment of this kind, a preliminary acidification step must be carried out.

The object of the present invention is to provide an enzymatic method for treating chemical lignocellulose pulps in order to separate out the lignin. The present invention makes it possible to eliminate the disadvantages of the aforementioned enzymatic treatment through a simplified implementation procedure which requires, in particular, neither preliminary acidification nor co-substrate.

SUMMARY OF THE INVENTION

It is an object of the present invention to provide a novel enzymatic method for treating chemical lignocellulose pulp in order to separate the lignin that requires neither preliminary acidification nor a co-substrate. The elimination of an acidification step and a co-substrate makes the present invention convenient and more cost effective over previously known enzymatic treatment methods of chemical lignocellulose pulp.

In one embodiment, the present invention relates to a method for treating a chemical lignocellulose pulp in a homogeneous aqueous suspension using an enzymatic preparation in a reactive median wherein the enzymatic preparation is derived from the bacterium *Streptomyces viridosporus* which enables a lignin-solubilizing action to occur in the absence of a co-substrate. This enzymatic preparation may also produce a hemicellulolytic activity.

In another embodiment, the present invention relates to the enzymatic method as described above wherein the chemical lignocellulose pulp is a kraft pulp.

In yet another embodiment, the present invention relates to the enzymatic treatment described above wherein the reactive medium has a pH of between 7 and 9 and preferably between 8 and 8.5. The reactive medium is heated to a temperature of between 20° C. and 65° C. and preferably between 35° C. and 40° C.

In another embodiment, the present invention relates to the enzymatic method described above wherein the enzymatic preparation is continued for a period of less than 8 hours. In another aspect of the present invention, the action of the enzymatic preparation is continued for a period of between 15 minutes and 3 hours.

In another embodiment, the present invention relates to the enzymatic treatment as described above wherein the concentration in mass percent of the pulp in the reactive medium is between 2 and 15% and preferably 4%.

In still another embodiment, the present invention relates to the enzymatic method described above wherein the lignin-solubilizing activity of the enzymatic preparation is between 0.001 and 0.1 U per gram of treated pulp.

In yet another embodiment, the present invention relates to the enzymatic method described above wherein the hemicellulolytic activity of the enzymatic preparation is a xylanase activity that is less than or equal to 20 U per gram of treated pulp.

In another embodiment, the present invention relates to the method of treatment described above wherein the bacteria *Streptomyces viridosporus* is taken from the strain referenced as ATCC 39115.

In a further embodiment, the present invention relates to the enzymatic method described above wherein after the activity produced by the enzymatic preparation is affected the pulp is washed in sodium carbonate. The pulp may additionally be washed in water after it is washed in sodium carbonate.

In yet another embodiment, the present invention relates to the method described above wherein the enzymatic treatment is repeated more than once.

In yet another embodiment, the present invention relates to the treatment method described above wherein the lignin is separated from the chemical lignocellulose pulp after the lignin solubilizing activity is affected.

In still another embodiment, the present invention relates to the method of enzymatic treatment described above wherein the treatment forms a component of a process for the manufacture of paper from chemical lignocellulose pulp. Furthermore the treatment may constitute at least one step of a bleaching procedure for the lignocellulose pulp.

Various other features and advantages of the present invention will become apparent from the drawing and the following detailed description of the invention.

DETAILED DESCRIPTION OF THE INVENTION

Figure 1:
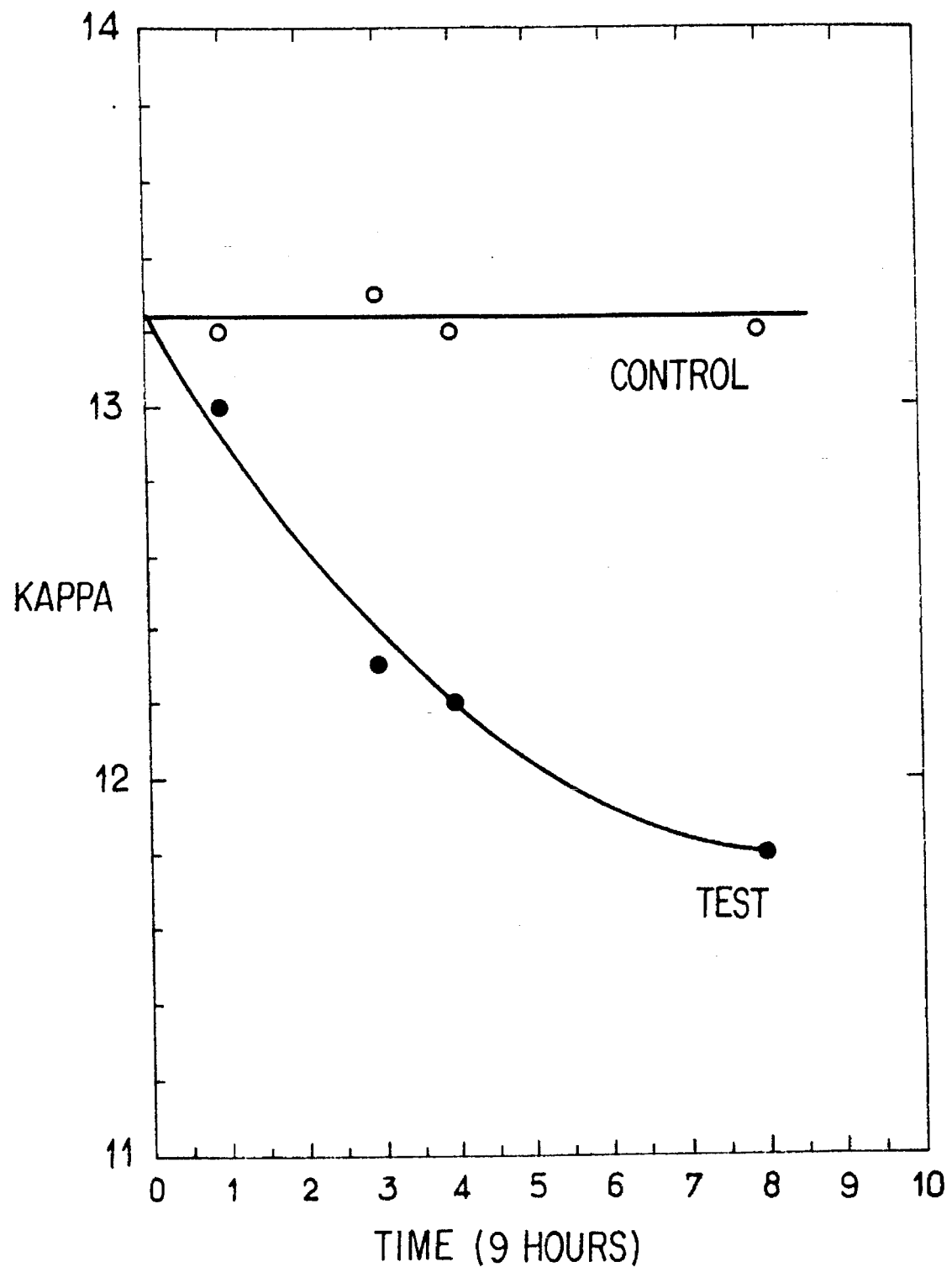
FIG. 1 shows the change in Kappa (Y axis) of the pulp as a function of time (X axis) of hardwood pulp that has undergone chemical treatment according to Example 5.

The purpose of the present invention is to provide a procedure for treating a chemical lignocellulose pulp in a homogeneous aqueous suspension using an enzymatic preparation derived from the bacterium *Streptomyces viridosporus* that produces a lignin-solubilizing action in the absence of a co-substrate.

This enzymatic preparation acts specifically on the lignin. However, the enzymatic preparation may, in addition to this activity, produce a hemicellulolytic action.

The treatment may be applied to all chemical lignocellulose pulps, and, in particular, to pulps treated with sulfate called kraft pulps.

During treatment with these enzymes, the reactive medium may be more or less suited to the action of these enzymes. For this reason, the pH and temperature conditions are more specifically adjusted for obtaining an optimal enzymatic activity, and also to avoid any risk of denaturing the enzymes.

According to the present invention, the pH of the reactive medium is between 7 and 9, and preferably, between 8 and 8.5. This latter range corresponds, moreover, to the growth pH of the microorganism-culture medium itself. This feature proves quite advantageous when the enzymatic treatment is used on kraft pulps removed from the chemical treatment because these pulps in solution already possess a basic pH greater than 8. Thus, the pulp may be treated directly without adjustment to an acidic pH. If necessary, the pH of the pulp in solution may be adjusted so as to obtain the optimal pH of 8 to 8.5 by adding, in particular, sodium carbonate or acid.

Treatment is carried out at a temperature generally ranging between 20° and 65° C., and preferably between 35° and 40° C. Like the pH, the latter narrower range which gives optimal enzymatic activity corresponds to the temperature range of the microorganism-culture medium, and also approximately to the temperature range observed for kraft pulps removed from the chemical treatment.

According to the present invention, the action of the enzymatic preparation continues for an interval generally less than 8 hours. This interval is chosen as a function of the activity, or activities, of the different enzymatic preparations derived from the bacterium *Streptomyces viridosporus*.

The percentage by weight of the pulp in suspension to be treated in relation to the aqueous solution containing the enzymatic preparation may vary quite widely. The percentage will advantageously range from 2 to 15%.

The solubilizing activity of the lignin in the enzymatic preparation used preferably ranges between 0.001 and 0.1 unit per gram of pulp (U/g).

Hemicellulolytic activity, and more specifically, the xylanase activity of the enzymatic preparation used, preferably range between 0 and 20 units per gram of pulp.

This enzymatic treatment makes it possible to separate out at least one part of the lignin contained in the lignocellulose pulp. The lignin-specific biodegradation products using *Streptomyces viridosporus* enzymes contain hydrosoluble polymers having an alkaline or neutral pH and a degree of polymerization less than that of the lignin itself. Thus, there is no biodegradation extending to complete mineralization of the lignin, however, the objective of the invention is achieved since the decomposition products can be easily separated out from the lignocellulose pulp, for example, by using simple spin drying.

Moreover, it was a surprising observation that this enzymatic preparation may produce considerable solubilizing activity on the lignin without requiring the presence of any co-substrate such as hydrogen peroxide. Prior to the present invention, the enzymes that have proven effective in their action on the lignin were mainly peroxidases which obligatorily require at least hydrogen peroxide to work. The treatment according to the present invention thus proves especially advantageous in view of the fact that without a co-substrate or other agent, implementation of the treatment is appreciably simplified, and less costly.

According to the present invention, treatment may be incorporated at different stages of the paper-manufacturing process. It may be incorporated into a conventional bleaching procedure, either as a preliminary step, a step interpolated between one of the sequences in the bleaching procedure, or as a step carried out after the procedure. The treatment may also be repeated several times.

According to the present invention, when the treatment is carried out prior to the bleaching procedure, it may prove advantageous, depending on the type of bleaching used, to follow the enzymatic treatment with a washing operation using sodium carbonate, followed by washing in water, as necessary.

This cycle involving enzymatic treatment/alkaline washing/washing in water may be repeated several times, i.e., 2 or 3 times, thereby increasing its effectiveness.

In addition, the enzymatic preparation according to the present invention may be used to treat the effluents flowing from an industrial paper plant.

The results obtained are explicit, especially as regards to bleaching, and will be described below. In all the cases described below by using the present invention of enzymatic treatment of chemical pulps, an appreciable increase in whiteness was observed as compared with the results obtained for a pulp which has been subjected only to the conventional bleaching operation, whether different bleaching procedures were implemented or a different initial type of wood (i.e., hardwood, coniferous, etc.) was used.

Furthermore, it is shown in the examples below that it is possible to reduce the proportion of active chlorine used, for example, during the first step D of an O-D-O-D-E-D-type bleaching procedure, by at least 25% while at the same time obtain improved whiteness, solely by means of a single enzymatic treatment carried out preliminarily to this bleaching operation.

It should also be noted that although the treatment makes it possible to enhance the whiteness of the paper, it in no way affects the paper's mechanical properties. In contrast, by conventional procedures, attempts to improve the final whiteness by implementing additional chemical steps within a bleaching procedure frequently cause reduced mechanical properties of the paper.

EXAMPLES

In all of the examples described, the features indicated are specified in the following manner:

The Kappa ($\kappa$) of a lignocellulose pulp makes it possible to assess the proportion of lignin in the pulp. Determination of this content, well known in the paper industry, is based on the principle of oxidation of the lignin in the pulp by means of potassium permanganate and is accurately furnished by Standard ISO-302. Knowledge of the Kappa of a pulp makes it possible to specify the mass percentage of active chlorine in relation to the pulp (indicated as Cl°) to be used during the first chlorination step of the bleaching procedure. The equation conventionally applied is: $Cl° = 0.2 \times \kappa$.

Whiteness is determined in accordance with Standard ISO-2470. It is the measurement of diffuse reflectance in the blue of the paper layer studied using a perfect reflected-light diffuser.

The actions of the enzymatic preparations derived from *Streptomyces viridosporus* are determined as follows:
Lignin-Solubilizing Activity The lignin-solubilizing activity of the enzymes is determined by placing an aqueous suspension of the enzymatic preparation in contact with lignocellulose in a powdered form called benzene alcohol powder (BAP). This powder is obtained by extracting lignocellulose from vegetable material in which the lignin has preliminarily and specifically been marked with carbon 14 according to a protocol specified in an article by G. Alibert and A. Boudet (1979, *Physiol.-Veg.* vol. 17, pages 67–74). This contact leads to the gradual solubilization of the radioactive compounds. These compounds are then analyzed. In practice, the lignocellulose powder is placed in suspension in a buffer of Tris/HCl (0.3M, pH 8.0 or 8.5) at a concentration of 10 mg/ml.

This suspension is added to the enzymatic solution (in the proportion of 1 volume to 3 volumes, respectively) while being stirred at 37° C. Monitoring of the reaction occurs by counting the radioactivity contained in the floating material in the samples of the medium taken over time. Results are expressed as a percentage of the radioactivity solubilized in relation to the initial radioactivity of the lignocellulose powder. This percentage directly gives the percentage of decomposed, solubilized lignin as compared to the initial lignin. It is agreed that one unit is defined as 1% of the radioactivity solubilized per minute.
Hemicellulolytic Activity The hemicellulolytic activity of the enzymatic preparation is based on the presence of xylanases in the preparation. The xylanases of *Streptomyces viridosporus* in contact with xylan release reducing sugars into the reactive medium, and these sugars are analyzed by the method utilizing 3,5-dinitrosalicylic acid (DNS) of J. B. Summer and S. F. Howell (1935, *J. Biol. Chem.*, vol. 108, pp. 51–54).

In practice, a 1% xylan solution (obtained by placing in solution at ambient temperature in a 0.1M phosphate buffer having a pH of 8) and the enzymatic preparation in solution are mixed in equal volumes while stirring at 37° C. or 50° C. The reaction is followed by measurement of the reducing sugars in samples drawn from the medium. These quantitative analyses may then be used to quantify the xylanase activity in units (U) according to international nomenclature.

The strain of *Streptomyces viridosporus* used here derives from that filed under Reference Number ATCC 39115. Culturing of the microorganism is undertaken conventionally in several stages, in an Erlenmeyer flask and then a fermentation vessel. Similarly, the bacteria are separated out in order to collect the extracellular medium containing the enzymes produced by the bacteria. The enzymes may then, if necessary, be purified and/or separated out.

In the examples described below, the enzymatic reaction occurred on a 4% lignocellulose pulp by weight in aqueous suspension containing the enzymatic preparation. As necessary, the pH of the suspension was adjusted to 8. Reaction occurred at 37° C. while stirring for a variable period extending up to 8 hours. At the end of the reaction, the pulp was spun dried and, as needed, washed with 1N sodium carbonate and then with water. When the pulp was next subjected to a bleaching procedure whose first sequence was an alkaline extraction under oxygen, washing in sodium carbonate was normally not performed.

All percentages given are mass percentages.

*Streptomyces viridosporus* Culturing Conditions

The *Streptomyces viridosporus* (S.v.) culturing steps used in Examples 1–4 are summarized briefly in the table below. Normal culturing conditions were used, i.e., at 37° C. under controlled oxygen pressure and at a pH of between 7.5 and 8.

| Step | Reaction Vessel | Seeding | Time (h) |
| --- | --- | --- | --- |
| 1 | Erlen 100 ml | 2 ml pellets stock | 24 |
| 2 | Erlen 1 l | S.v. in step 1, ground | 12 |
| 3 | Braun | S.v. in step 2 | 12 |

Next, the culture medium was filtered over silicate/glass fiber membranes to remove the microorganisms. The filtrate was then concentrated and a first separation of the different enzymes was carried out by placing the enzymes in solution in contact with an ion-exchange gel (C.M. sepharose), the solution being buffered to pH 5 (20 mM citrate). The enzymes not bonded to the gel were brought together in a fraction termed the floating fraction and gathered by filtration and rinsing of the gel. This floating fraction makes it possible to treat three different types of lignocellulose pulps.

The lignin-solubilizing activity of this floating fraction was 0.5 unit per liter of enzymatic preparation (U/l) and the xylanase activity, 100 U/l.

EXAMPLE 1

The enzymatic treatment was carried out at a pH of 8, and at 37° C. for 120 mn on a kraft pulp derived from deciduous wood such as oak, beech, chestnut, poplar, or a mixture of these, and this pulp subsequently underwent a bleaching operation whose sequences were as follows:

chlorination step C: $Cl°=0.2\times Kappa$
alkaline extraction step E: NaOH=2%
hypochlorite-reaction step H: $Cl°=1.5$
chloride dioxide-reaction step DF: $Cl°=1\%$.

The following results as shown in Table I were obtained:

TABLE I

| | Control | With enzymatic treatment |
| --- | --- | --- |
| Kappa after treatment | 12.8 | 11.3 |
| Whiteness at D | 87.4 | 88.1 |

EXAMPLE 2

The same treatment under the same conditions was repeated on a kraft pulp made from coniferous wood such as Norway spruce and/or fir, which then underwent a bleaching treatment whose sequences were the following:

the step C/D, i.e., using a mixture of chlorine and chlorine dioxide: $Cl°=0.18\times Kappa$ (20% $ClO_2$)
a step $E_1$: NaOH=2.5%
a step $D_1$: $Cl°=3\%$
a step $E_2$: NaOH=1%
a step $D_2$: $Cl°=1.5\%$.

The following results as shown in Table II were obtained.

TABLE II

| | Control | With enzymatic treatment |
| --- | --- | --- |
| Kappa after treatment | 25.6 | 23 |
| Whiteness at $D_1$ | 66.4 | 71.5 |
| Whiteness at $D_2$ | 85 | 86.7 |

EXAMPLE 3

The enzymatic treatment was conducted as in the preceding examples, this time also on a coniferous kraft pulp, in this instance obtained from maritime pine and whose subsequent bleaching procedure included the following steps:

an attack step $O_1$ under oxygen in an alkaline medium: $P(O_2)=3$ bars, NaOH=2.55
a step $D_1$: $Cl°=0.2\times Kappa$
a step $O_2$: $P(O_2)=3$ bars, NaOH=2%
a step $D_2$: $Cl°=2\%$
a step E: NaOH=1%
a step $D_3$: $Cl°=1\%$.

The following results as shown in Table III were obtained:

TABLE III

| | Control | With enzymatic treatment |
| --- | --- | --- |
| Kappa after treatment | 29.9 | 27.63 |
| Kappa after $O_1$ | 16.9 | 15.1 |
| Kappa after $O_2$ | 4.2 | 3.9 |
| Whiteness at $D_2$ | 78.6 | 79.7 |
| Whiteness at $D_3$ | 90.7 | 91.8 |

EXAMPLE 4

The nature of the pulp, the enzymatic treatment, and the bleaching procedure were virtually the same as those given in Example 3. The only difference was that in bleaching step $D_1$, active chlorine $Cl°$ was used in the following quantity: $Cl°=0.15×\kappa$, i.e., approximately 25% less active chlorine was used for this step.

The following results as shown in Table IV were obtained:

TABLE IV

|  | Control | With enzymatic treatment |
|---|---|---|
| Kappa after $O_2$ | 4.7 | 4.3 |
| Whiteness at $_2$ | 76.5 | 77.7 |
| Whiteness at $D_3$ | 89.9 | 91.1 |

These examples show that for the three types of pulp employed, improvement of whiteness was very substantial, i.e., approximately 1 to 2% whiteness after bleaching and approximately 1 to 2 points over this value of Kappa just after enzymatic treatment. These are totally advantageous improvements, since it is rather difficult to obtain increased whiteness beyond a whiteness level of approximately 85 to 90%.

Examples 3–4 further show that by using 25% less active chlorine in step $D_1$ of the bleaching operation cited, a whiteness not only equivalent, but greater, is obtained as a result of the enzymatic treatment since a definitive whiteness of 91.1 was achieved in Example 4, while the whiteness of the control in Example 3 was merely 90.7.

This signifies that a choice may be made, either to focus the objective on a maximum whiteness by retaining the conventional proportion of chlorine used in the bleaching procedure, or on a very considerable reduction of the conventional proportion of chlorine while maintaining satisfactory whiteness. Other objectives between these two limits may also be contemplated.

EXAMPLES 5–6

In Examples 5 and 6, the bacteria culturing steps were identical. Similarly, after culturing, a filtration of the bacteria was carried out and the filtrate was concentrated without performing any analytic separation.

The lignin-solubilizing activity of the enzymatic solution was 0.8 U/l.

EXAMPLE 5

A hardwood pulp which had just undergone chemical treatment using the above enzymatic solution at a temperature of 37° C. and a pH of 8.7 was treated. The change in the Kappa of the pulp was measured as a function of time (0–8 hours), the initial Kappa being approximately 13.2 as compared with a control. The curve obtained is given in the FIG. 1. A clear lowering of the Kappa was observed, the Kappa reaching approximately 11.9 after 8 hours, i.e., an increase of 1.3 points.

EXAMPLE 6

An identical pulp was treated in the same way as Example 5 except for the time which was decreased to four hours. The pulp was then washed in 1N sodium carbonate. The same treatment was repeated once again. The change in Kappa as a function of the number of treatments is given in Table V below:

TABLE V

| Enzymatic treatment | |
|---|---|
| Kappa before the first treatment: | 13.9 |
| Kappa after the first treatment: | 12.1 |
| Kappa after the second treatment: | 10.1. |

It was found that by performing the enzymatic treatment twice in succession, the value of Kappa could be appreciably improved.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of bleaching lignocellulose pulp, comprising the steps of:

(1) mixing a lignocellulose pulp in a homogeneous solution with an enzymatic preparation in a reactive medium having a pH of between 7 and 9, wherein said enzymatic preparation is obtained by culturing *Streptomyces viridosporus* bacteria in a culture medium, removing said bacteria from said cultured medium to obtain an enzyme-containing solution, contacting said enzyme-containing solution with a carboxymethylcellulose ion exchange gel at pH 5 and then separating said gel from said solution to obtain said enzymatic preparation, wherein said enzymatic preparation comprises at least one enzyme having a lignin-solubilizing activity between 0.01 and 0.1 U per gram of treated pulp and a xylanase activity of 0–20 U per gram of treated pulp, to obtain a treated pulp; and (2) bleaching said treated pulp.

2. The method of claim 1, wherein said bleaching step comprises contacting said treated pulp with chlorine, chlorine dioxide or a mixture thereof.

3. The method of claim 1, further comprising contacting said treated pulp with chlorine, chlorine dioxide or a mixture thereof to produce a chlorinated pulp, extracting said chlorinated pulp with an alkaline solution to form an extracted pulp.

4. The method of claim 1, further comprising contacting said treated pulp with a sodium carbonate solution.

5. The method of claim 1, wherein said pH is between 8 and 8.5.

6. The method of claim 1, wherein said mixing is conducted at a temperature between 35° C. and 40° C.

7. The method of claim 1, wherein said bacterium is *Streptomyces viridosporus* strain ATCC 39115.

8. The method of claim 1, wherein said enzymatic preparation has a lignin-solubilizing activity of 0.5–0.8 U/l.

9. The method of claim 1, further comprising repeating step (1).

* * * * *